United States Patent
Kim

(10) Patent No.: US 10,150,799 B2
(45) Date of Patent: Dec. 11, 2018

(54) **SIALIC ACID-SPECIFIC BINDING AFFINITY LECTIN FROM THE MUSHROOM *HERICIUM ERINACEUM***

(71) Applicant: KOREA RESEARCH INSTITUTE OF BIOSCIENCE AND BIOTECHNOLOGY, Daejeon (KR)

(72) Inventor: Seounghun Kim, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 205 days.

(21) Appl. No.: 15/158,407

(22) Filed: May 18, 2016

(65) Prior Publication Data

US 2016/0326223 A1 Nov. 10, 2016

Related U.S. Application Data

(63) Continuation of application No. PCT/KR2014/010974, filed on Nov. 14, 2014.

(30) Foreign Application Priority Data

Nov. 18, 2013 (KR) ................. 10-2013-0140244
Nov. 14, 2014 (KR) ................. 10-2014-0158614

(51) Int. Cl.
  *C07K 14/375* (2006.01)
  *C07K 14/37* (2006.01)
  *G01N 33/58* (2006.01)
  *G01N 33/68* (2006.01)

(52) U.S. Cl.
  CPC ............ *C07K 14/375* (2013.01); *C07K 14/37* (2013.01); *G01N 33/582* (2013.01); *G01N 33/6848* (2013.01); *G01N 2333/42* (2013.01)

(58) Field of Classification Search
  None
  See application file for complete search history.

(56) References Cited

U.S. PATENT DOCUMENTS 8,461,305 B2  6/2013  Kobayashi et al.
2006/0251580 A1  11/2006  Keppler et al.

FOREIGN PATENT DOCUMENTS

| EP | 2 078 755 A1 | 7/2009 |
| JP | 2010-091308 | 4/2010 |
| JP | 2010-256132 | 11/2010 |
| JP | 2012-219064 | 11/2012 |
| KR | 1020040061963 A | 7/2004 |
| WO | WO 2002094869 A1 | 11/2002 |
| WO | WO 2010/010674 | 1/2010 |

OTHER PUBLICATIONS

Kawagishi et al. "A sialic acid-binding lectin from the mushroom *Hericium erinaceum*" *FEBS Letters* 340:56-58 (1994).

Pohleven et al. "Affinity Chromatography of Lectins" *Affinity Chromotography* p. 49-74 (2012).

Li et al. "A Novel Lectin with Antiproliferative and HIV-1 Reverse Transcriptase Inhibitory Activities from Dried Fruiting Bodies of the Monkey Head Mushroom *Hericium erinaceum*," *Journal of Biomedicine and Biotechnology* 2010:1-9 (2010).

*Primary Examiner* — Marsha Tsay
(74) *Attorney, Agent, or Firm* — Klarquist Sparkman, LLP

(57) ABSTRACT

The present invention concerns lectins isolated from the fruiting body of a novel *Hericium erinaceum* (deposit number: KCTC 12499BP) NEU-1L strain which bind specifically to sialic acid. The invention further pertains to uses of such lectinsn abd to processes for their preparation thereby. The lectin of the present invention can be useful as an active ingredient of a composition or a kit for measuring or detecting glycoproteins, glycopeptides, glycolipids, sugar precursors or oligosaccharides containing sialic acid moieties, or further for measuring or detecting cell lines, bacteria and viruses containing sialoglycoconjugates.

5 Claims, 8 Drawing Sheets

Specification includes a Sequence Listing.

[Fig.1]
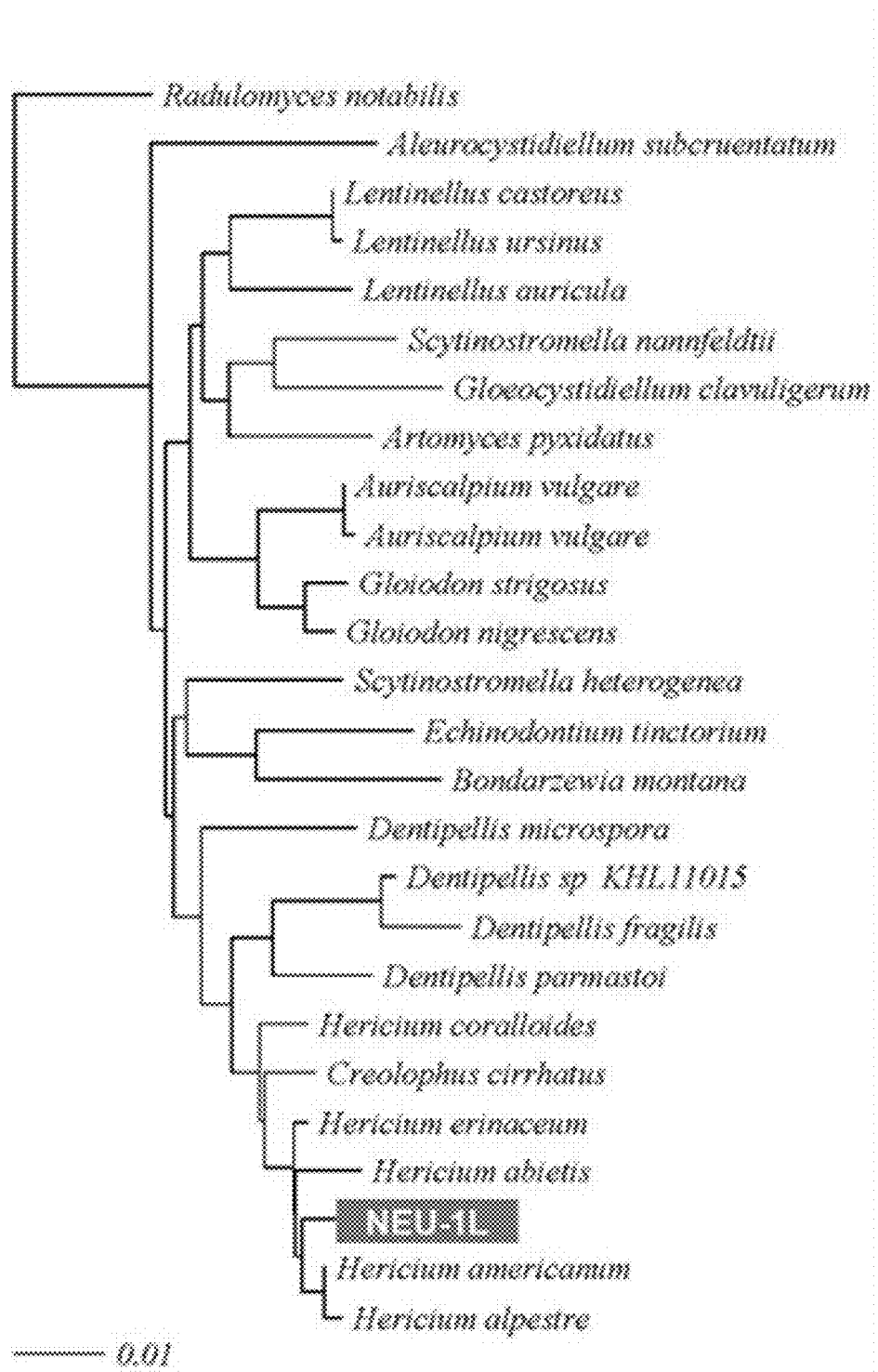

[Fig.2]
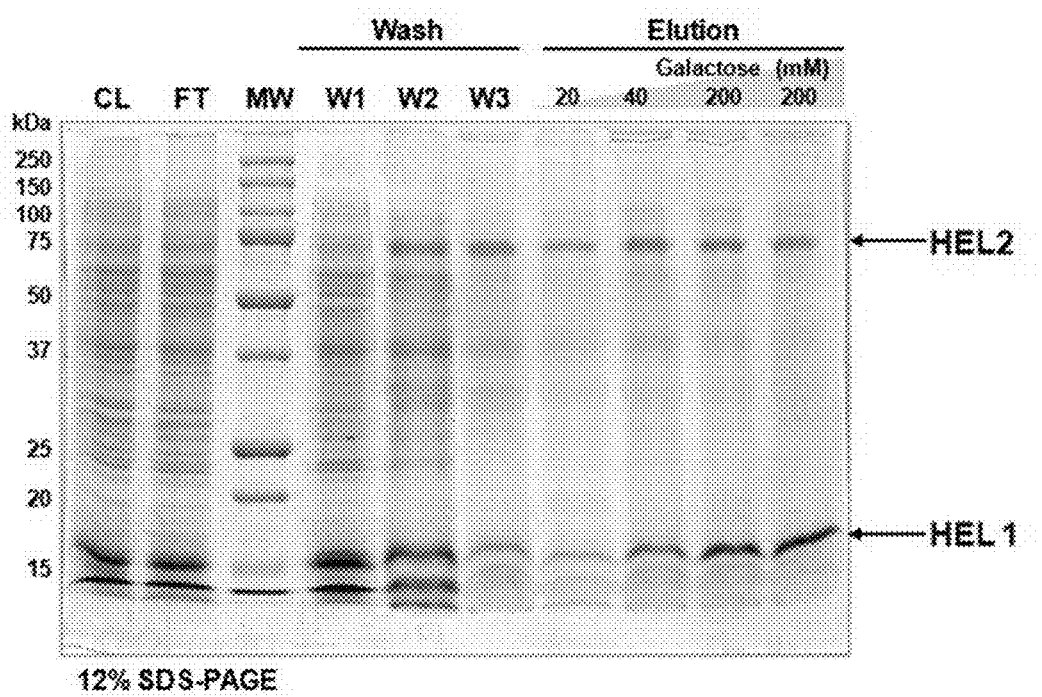

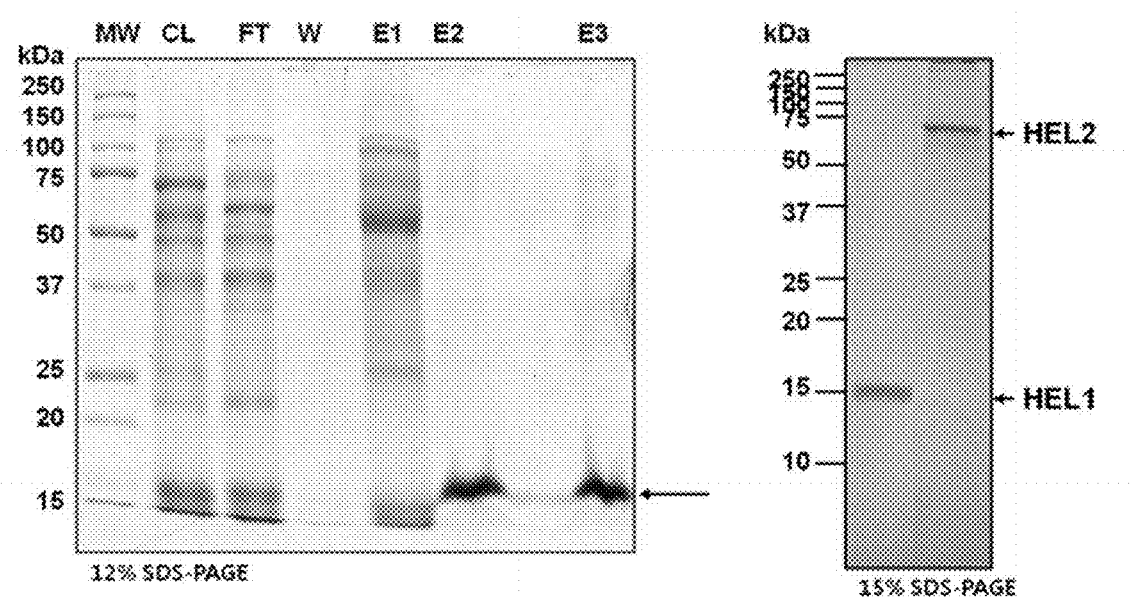
[Fig.3]

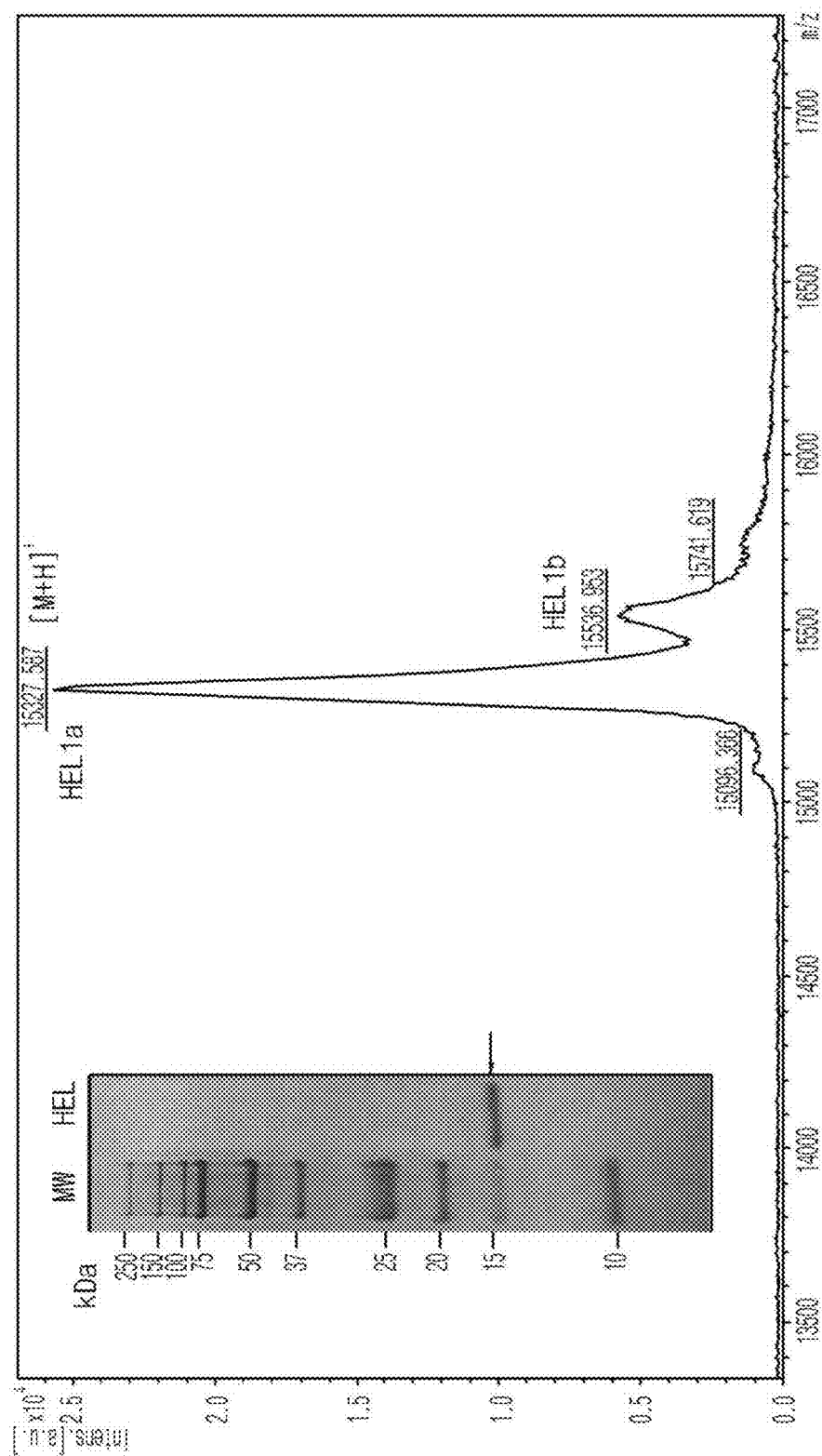

[Fig. 5A]
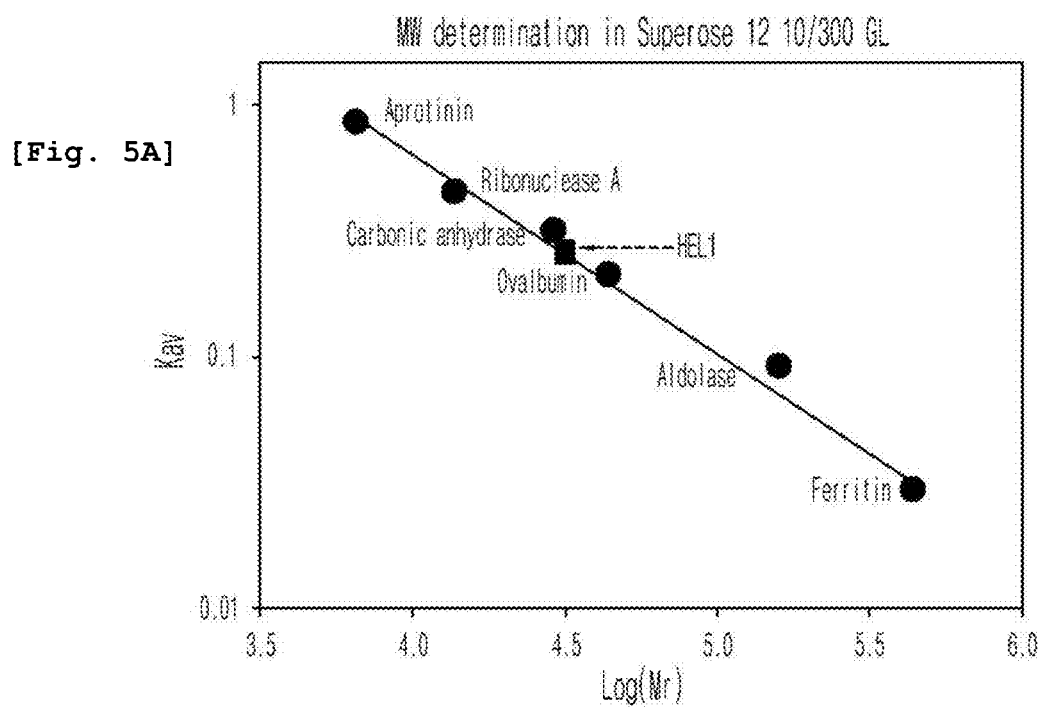
[Fig. 5B]
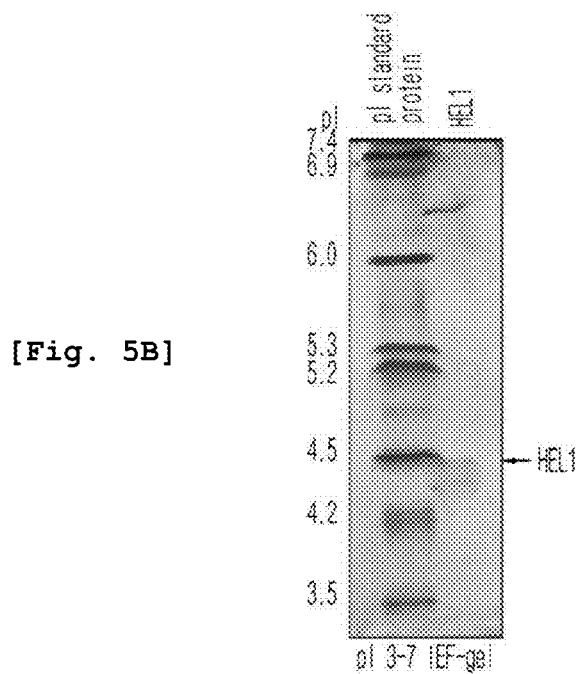

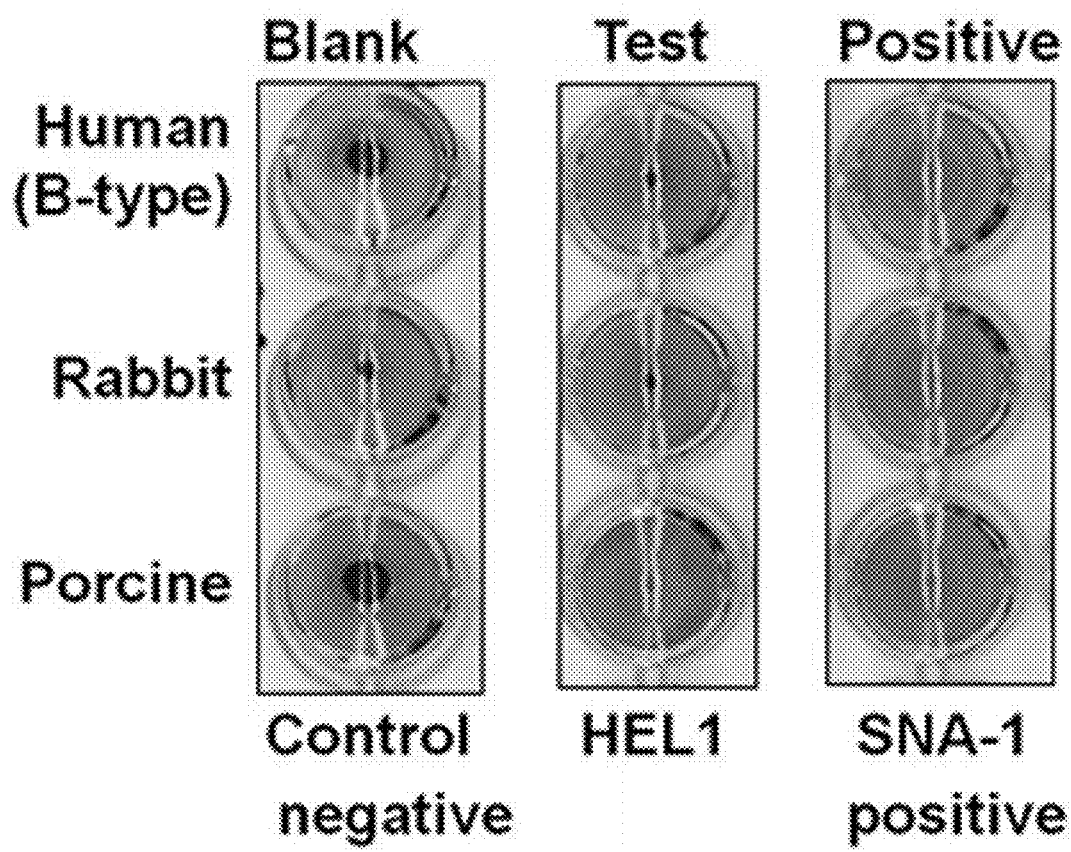
[Fig.6]

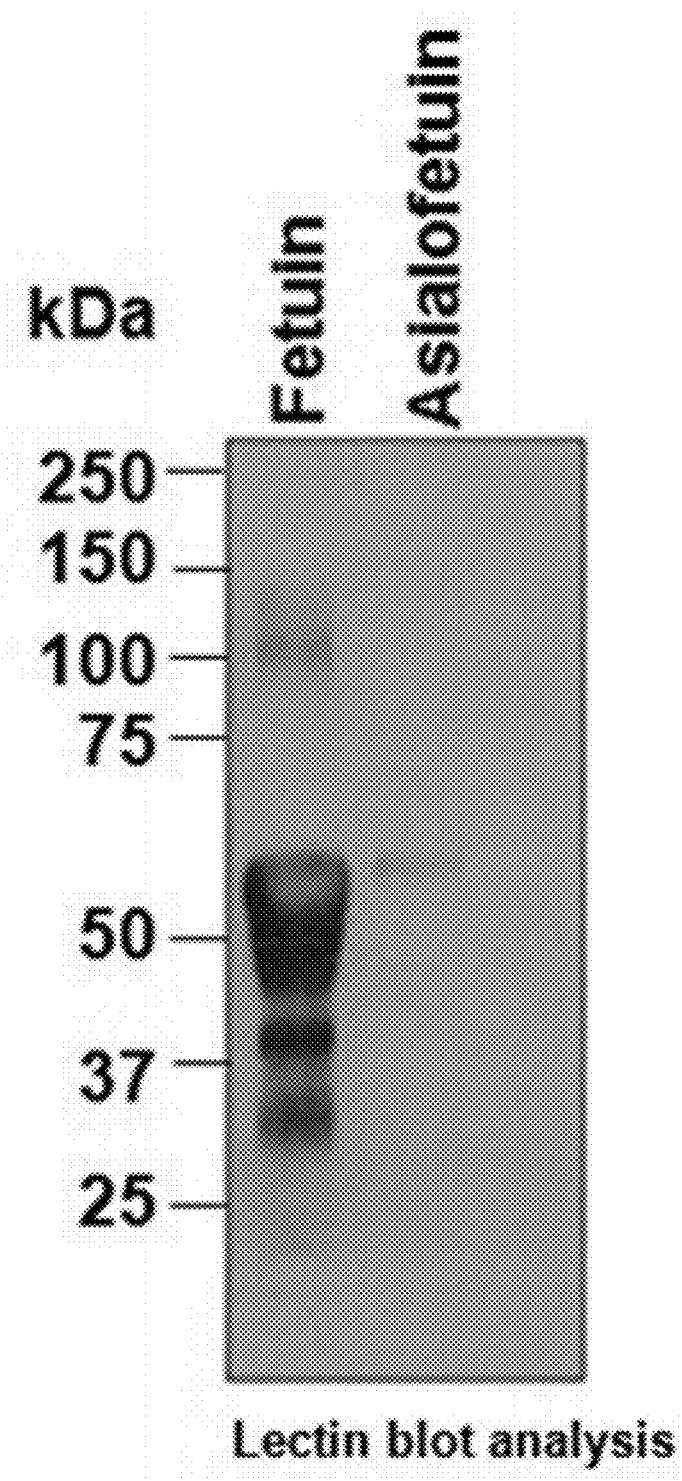

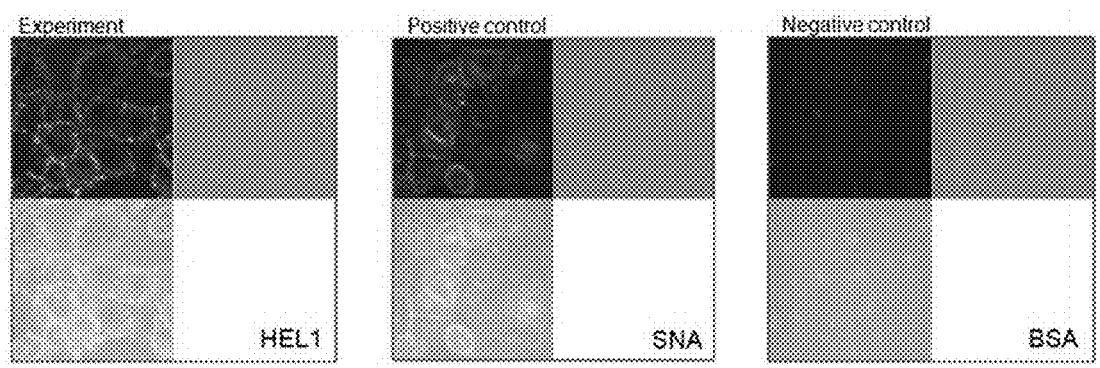
[Fig.8]

SEQUENCE LISTING

<160> NUMBER OF SEQ ID NOS: 9

<210> SEQ ID NO 1
<211> LENGTH: 1146
<212> TYPE: DNA
<213> ORGANISM: Hericium erinaceum

<400> SEQUENCE: 1

```
actagtgatt cgccagttct gcttaccaaa aatgcccac tagaaactct caatcgccaa      60
gcggtccaat caagtgacgg cttgttctta catatttaaa gtttgagaat aggttaaggt     120
tgtttcaacc ccaaggcctc taatcattcg ctttaccaca taaatctgat atgagtttct     180
gctatcctga gggaaacttc ggcaggaacc agctactaga tggttcgatt agtctttcgc     240
ccctataccc aaatttgacg gtcgatttgc acgtcagaat cgctacgagc ctccaccaga     300
gtttcctctg gcttcaccct attcaggcat agttcaccat ctttcggatc ccaacataca     360
cgctctaccg cagatccgtc acagaaggtc tggtccgggc gtcggtgccc tccataacag     420
aggtcccaac tttcactttc attacgcgca cgggttttcc acccgaacac tcgcgggcat     480
gttagactcc ttggtccgtg tttcaagacg ggtcgtttaa agccattacg ccagcatcct     540
aagcatgaac gtgggcgaac cccgaccata aaggcatgct gaattcctca atcccaacca     600
ccgtatacga ctggaggcta taacacaccc gaaggtgcca cattccccca gcccttgtcc     660
ggcagtcgaa attgatgctg gcccgtccac cagaaaatac accaggcaag attgcaaggc     720
tgagttctgg cggacgcgac tgacttcaag cgtttccctt tcaacaattt cacgtactgt     780
ttaactctct ttccaaagtg cttttcatct ttccctcacg ggtacttgtt cgctatcggg     840
tctctcgcca atatttagct ttagatggaa ttcaccaccc attttgagct gcattcccaa     900
acaactcgac tctttgagag cgcatcacag agcactggta gtccgtgtca aagacgggat     960
tctcaccctc tatgacgctc cattccagga gacttgtaca cggtccagcg cggaaagcac    1020
ttctccagac tacaactcgg acggccaaag accgccagat tttaaatttg agcttttccc    1080
gcttcactcg cagttactag gggaatcctt gttagtttct tttcatccgc ttattgatat    1140
gcaatc                                                              1146
```

<210> SEQ ID NO 2
<211> LENGTH: 24

```
<212> TYPE: DNA
<213> ORGANISM: Artificial Sequence
<220> FEATURE:
<223> OTHER INFORMATION: NL1 primer

<400> SEQUENCE: 2
gcatatcaat aagcggagga aaag                                           24

<210> SEQ ID NO 3
<211> LENGTH: 17
<212> TYPE: DNA
<213> ORGANISM: Artificial Sequence
<220> FEATURE:
<223> OTHER INFORMATION: LR6 primer

<400> SEQUENCE: 3
cgccagttct gcttacc                                                   17

<210> SEQ ID NO 4
<211> LENGTH: 644
<212> TYPE: DNA
<213> ORGANISM: Artificial
<220> FEATURE:
<223> OTHER INFORMATION: ITS1-5.8S-ITS4 rDNA sequencing

<400> SEQUENCE: 4
actagtgatt tccgtaggtg aacctgcgga aggatcatta atgaatttga aaggagttgt    60
tgctggcctg aaacccaggc atgtgcacgc tccaatctca tccatcttac acctgtgcac   120
ccttgcgtgg gtccgtcggc tttgcggtcg atgggcttgc gttttcata aactcttatg    180 tatgtaacag aatgtcataa tgctataaac gcatcttata caactttcaa caacggatct   240
cttggctctc gcatcgatga agaacgcagc gaaatgcgat aagtaatgtg aattgcagaa   300
ttcagtgaat catcgaatct tgaacgcac cttgcgcccc ttggtattcc gaggggcacg    360
cctgttcgag tgtcgtgaaa ttctcaactc aatcctcttg ttatgagagg ctgggcttg    420 gacttggagg tcttgccggt gctccctcgg gaagtcggct cctcttgaat gcatgagtgg   480 atccctttg tagggtttgc ccttggtgtg ataattatct acgccgcggg tagccttgcg    540
ttggtctgct tctaaccgtc ttcggacaac tttcatctca acttgacctc gaatcaggcg   600
ggactacccg ctgaacttaa gcatatcaat aagcggagga aatc                    644

<210> SEQ ID NO 5
<211> LENGTH: 19
<212> TYPE: DNA
<213> ORGANISM: Artificial
<220> FEATURE:
<223> OTHER INFORMATION: ITS1

<400> SEQUENCE: 5
tccgtaggtg aacctgcgg                                                 19

<210> SEQ ID NO 6
<211> LENGTH: 20
<212> TYPE: DNA
<213> ORGANISM: Artificial
<220> FEATURE:
<223> OTHER INFORMATION: ITS4

<400> SEQUENCE: 6
tcctccgctt attgatatgc                                                20

<210> SEQ ID NO 7
```

```
<211> LENGTH: 11
<212> TYPE: PRT
<213> ORGANISM: Artificial
<220> FEATURE:
<223> OTHER INFORMATION: HEL1a_strong

<400> SEQUENCE: 7

Lys Glu Pro Thr Val Trp Gly Arg Pro Glu Ser
1               5                   10

<210> SEQ ID NO 8
<211> LENGTH: 11
<212> TYPE: PRT
<213> ORGANISM: Artificial
<220> FEATURE:
<223> OTHER INFORMATION: HEL1b_weak

<400> SEQUENCE: 8

Trp Pro Val Ala Pro Asp Tyr Pro Pro Glu Ser
1               5                   10

<210> SEQ ID NO 9
<211> LENGTH: 30
<212> TYPE: PRT
<213> ORGANISM: Artificial
<220> FEATURE:
<223> OTHER INFORMATION: 50_75 kDa N-terminal amino sequence

<400> SEQUENCE: 9

Gly Gly His Ser Val Pro Leu Thr Asn Phe Met Asn Ala Gln Tyr Phe
1               5                   10                  15

Thr Glu Ile Ser Leu Gly Ser Pro Pro Gln Gln Phe Lys Val
            20                  25                  30
```

SIALIC ACID-SPECIFIC BINDING AFFINITY LECTIN FROM THE MUSHROOM *HERICIUM ERINACEUM*

CROSS REFERENCE TO RELATED APPLICATION

This patent application is a continuation of PCT/KR2014/010974, filed Nov. 14, 2014, which claims the benefit of priority from Korean Patent Application No. 10-2014-0158614, filed on Nov. 14, 2014 and Korean Patent Application No. 10-2013-0140244, filed on Nov. 18, 2013. The contents of all three of these patent applications are incorporated herein by reference.

BACKGROUND OF THE INVENTION

1. Field of the Invention

The present invention relates to a novel *Hericium erinaceum* NEU-1L strain (deposit number: KCTC 12499BP), a lectin binding specifically to sialic acid which is produced thereby, and a use of the same.

2. Description of the Related Art

Lectin is one of the proteins that can bind to glycoconjugates, which is endogenous in a variety of organisms from microorganisms to higher animals. It is known that lectin is involved in various life phenomena including protein quality control, host-pathogen interaction, cell-cell communication, inflammation, immune response, cancer progression, and development by binding specifically to glycoconjugates (Lam and Ng, 2011. Appl. Microbiol. Biotechnol. 89, 45).

Lectins are multivalent carbohydrate binding proteins that display neither catalytic activity nor antibody like characteristics. Lectin was first isolated from *Ricinus communis* by the Russian scientist Sillmark in the late 19$^{th}$ century. Since then, 40 kinds of lectins including Concanavlain A (ConA) have been identified, studied, and used in various fields. According to the recent advancement of molecular biology and biochemistry, lectins are classified into many groups according to their nucleotide sequences and protein structures. According to origin, lectins are also classified into plant lectin (plant lectin families) and animal lectin (invertebrate/vertebrate lectin families). Vertebrate lectins are divided into such groups as C-type (mannose-binding lectin, MBL), S-type (galectin: β-galactoside-binding lectin), P-type (mannose-6-phosphate bind lectin), and I-type (selectin) according to their characteristics, and belongs to the Pentraxin group represented by a cyclic pentameric structure according to their protein structure. In spite of such an abundance of lectin, invertebrate/vertebrate lectin families functioning somehow in physiological metabolism in cells have been rarely reported, compared to plant lectins. Therefore, plant lectins extracted from the natural system have been widely applied to diagnose blood type and applied thereof by using their glycan binding specificities (Lehmann et al., 2006, Cell. Mol. Life Sci. 63, 1331).

Plant lectins are identified in almost every part of a plant including leaves, stems, roots, flowers, and pollens, and even in seeds and bulbs which can be harvested. Therefore, plant lectins have been easily purified from plants. In plants, lectins are involved in a variety of activities and functions such as immune function, self-defense from harmful insects, self-defense from animals by causing allergic reaction, anti-fungal activity, anti-viral activity, colonization in a specific region of symbiotic microorganism by cell/cell interaction between plants and microorganisms, delivery and preservation of nutrients and metal ions, protecting plants from coldness, acting as a partner to increase enzyme activity in cells, and trafficking of glycoproteins, etc. These activities and functions are accomplished by glycan specific binding activities of lectins, according to the previous reports (Lehmann et al., 2006, Cell. Mol. Life Sci. 63, 1331; Singh et al., 2010 Crit. Rev. Biotechnol. 30, 99).

By using such a glycoconjugate specific binding activity of a lectin, a lectin is believed to be effectively used for the early diagnosis of a specific disease by observing the changes of glycoproteins, glycolipids, and oligosaccharides presented on the cell surface, and further studied with animal tests to cope with a disease by boosting the in vivo immune system by the agglutination with glycoconjugates of the cell surface of the key cells to cause a disease or of the cell surface of viruses and microorganisms. Along with the recent development of optical microscope techniques and the chemical synthesis methods of various fluorescent probes, the glycan specific binding activity of lectin is a useful tool for application of glycan biomarker detection for the early diagnosis of cancer cells, the identification of the location of a specific endogenous glycoprotein, the measurement of glycan-mediated cell/cell interaction, and scanning of image of intracellular invasion of viruses and microorganisms, owing to its usability in recognizing glycoconjugates on the surface of specific cells, viruses, and microorganisms. The commercialized lectins nowadays are extracted from various sources such as plants, animals, and microorganisms, and they are useful for measuring the basic monomer of sialic acid (Neu5Ac, N-acetaylneuraminic acid), galactose (Gal), N-acetylglucosamine (GlcNAc), N-acetylgalactosamine (GalNAc), fucose (Fuc), mannose (Man), rhamnose (Rha), xylose (Xyl), and glucose (Glc) (Lehmann et al., 2006, Cell. Mol. Life Sci. 63, 1331; Singh et al., 2010 Crit. Rev. Biotechnol. 30, 99; Kajiwara et al., 2010, Microbes Environ. 25, 152).

However, owing to the variety of glycan structures including alpha-linkage and beta-linkage, and monomer composition of glycans, hundreds of or thousands of different glycan structures can be theoretically found in a natural system. Nevertheless, the number of lectins identified so far are limited to detect or to measure these types of glycoconjugates. In particular, the commercialized Maackia amurensis (MAA), Sambucus nigra (SNA), and Limulus polyphemus lectins are known to bind specifically to the specific sialic acid (Neu5Ac). However, a limited number of sialic acid-binding lectins are available rather than other sugar binding proteins for Gal and GlcNAc, etc. In addition, these sialic acid binding lectins sometimes do not distinguish α(2,3)-, α(2,6)-, and α(2,8)-sialic acid linkages precisely, due to non-specific binding activities.

SUMMARY

Therefore, the present inventors tried to develop a novel lectin binding specifically to sialoglycoconjugates. As a result, the inventors obtained a novel active lectin protein through a purification process from *Hericium erinaceum* (deposit number: KCTC 12499BP). The present inventors finally completed this invention by confirming that the novel lectin protein can be widely applied to the study of life phenomena mediated by sugar chains and also to the measurement of cells, proteins, and glycoconjugates having sialic acid moieties such as glycoproteins, glycolipids, and oligosaccharides, and to the monitoring of a microorganism containing sialoglycoconjugates.

It is an object of the present invention to provide a novel *Hericium erinaceum* NEU-1L strain (deposit number: KCTC 12499BP).

It is another object of the present invention to provide a method for producing a lectin, which binds specifically to glycoconjugates, from a fruiting body of a novel *Hericium erinaceum* NEU-1L strain (deposit number: KCTC 12499BP); and a lectin produced thereby.

It is also an object of the present invention to provide a composition or a kit for the measurement or detection of glycoproteins, glycopeptides, glycolipids, sugar precursors, or oligosaccharides having sialic acid moieties, including the lectin of the invention binding specifically to sialic acid.

It is further an object of the present invention to provide a composition or a kit for the measurement or detection of cell lines, bacteria, or viruses containing sialoglycoconjugates, including the lectin of the invention binding specifically to sialic acid.

To achieve the above objects, the present invention provides a novel *Hericium erinaceum* NEU-1L strain (deposit number: KCTC 12499BP).

The present invention also provides a method for preparation of a lectin, which binds specifically to sialic acid, from a fruiting body of a novel *Hericium erinaceum* NEU-1L strain (deposit number: KCTC 12499BP); and a lectin produced thereby.

The present invention also provides a composition or a kit for the measurement or detection of glycoproteins, glycopeptides, glycolipids, sugar precursors, or oligosaccharides having sialic acid moieties, including the lectin of the invention binding specifically to sialic acid.

The present invention also provides a composition or a kit for the measurement or detection of cell lines, bacteria, or viruses having sialic acid sialoglycoconjugates, including the lectin of the invention binding specifically to sialic acid.

The present invention also provides a use of the kit for the measurement or quantification of glycoproteins, glycopeptides, glycolipids, sugar precursors, or oligosaccharides having sialic acid moieties, including the lectin of the invention.

The present invention also provides a use of the kit for the monitoring, measurement or quantification of cell lines, bacteria, or viruses having sialic acid sialoglycoconjugates, including the lectin of the invention.

ADVANTAGEOUS EFFECT

The present invention provides a method for producing a lectin, which binds specifically to sialoglycoconjugates, wherein the lectin is from a fruiting body of a novel *Hericium erinaceum* (deposit number: KCTC 12499BP) NEU-1L strain; and a lectin produced thereby. The lectin of the present invention can be useful as an active ingredient of a composition or a kit for measuring or detecting glycoproteins, glycopeptides, glycolipids, sugar precursors or oligosaccharides having sialic acid moieties, containing a lectin specifically binding to sialic acid, or a composition or a kit for measuring or detecting cell lines, bacteria and viruses having sialoglycoconjugates, containing a lectin specifically binding to sialic acid moieties.

BRIEF DESCRIPTION OF THE DRAWINGS

The application of the preferred embodiments of the present invention is best understood with reference to the accompanying drawings, wherein:

FIG. 1 is a diagram illustrating the phylogenetic tree represented as evolutionary relationship between 26S rDNA of the *Hericium erinaceum* NEU-L1 strain and that of the similar strain.

FIG. 2 is a diagram illustrating the result of SDS-PAGE with the lectin purified from the *Hericium erinaceum* fruiting body by using fetuin-conjugated agarose column;
CL: cell extract;
FT: non-bound, flow through fraction;
MW: standard protein marker;
Wash W1: column wash fraction 1;
Wash W2: column wash fraction 2;
Wash W3: column wash fraction 3;
Elution 20: fraction eluted at 20 mM galactose;
Elution 40: fraction eluted at 40 mM galactose; and
Elution 200: fraction eluted at 200 mM galactose.

FIG. 3 is a diagram illustrating the results of 12% SDS-PAGE and 15% SDS-PAGE with the lectin proteins purified from the *Hericium erinaceum* fruiting body in each phase (left) and HEL1 and HEL2 lectin proteins (right), purified from the above by using DEAD-Sepharose column, Fetuin-agarose column, and Superose 12 column;
MW: standard protein marker;
CL: cell extract;
FT: non-bound, flowthrough fraction;
W: DEAE-Sepharose column wash fraction;
E1: fraction eluted from DEAE-Sepharose column;
E2: fraction eluted from Fetuin-agarose column; and
E3: fraction eluted from Superose 12 column.

FIG. 4 is a diagram illustrating the result of 16% Tricine-PAGE with the purified HEL1 lectin and the molecular weights of the two lectin proteins HEL1a and HEL1b included in HEL1 lectin which was measured by MALDI-TOF MS;
MW: standard protein marker; and
HEL: HEL1 lectin protein.

FIGS. 5A and 5B are a set of diagrams illustrating the size of the HEL1 protein purified by Superose 12 column under non-denaturing condition (FIG. 5A) and the pI value of HEL1 lectin in pI 3~7 IEF-gel (FIG. 5B);
pI standard protein: standard protein pI marker; and
HEL1: HEL1 lectin protein.

FIG. 6 is a diagram illustrating the agglutination activity of HEL1 lectin protein towards human, rabbit, and porcine erythrocytes;
Human (B-type): human erythrocyte (blood type: B);
Rabbit: rabbit erythrocyte;
Porcine: porcine erythrocyte;
Blank, Control negative: negative control;
Test, HEL1: experimental group, HEL1 lectin; and
Positive, SNA-1 positive: positive control, SNA-1 lectin.

FIG. 7 is a diagram illustrating the binding affinity of HEL1 purified from the *Hericium erinaceum* fruiting body to a sialylated protein fetuin measured by lectin blotting analysis;
Fetuin, sialylated glycoprotein;
Asialofetuin, non-sialylated glycoprotein.

FIG. 8 is a diagram illustrating the detection of A549 cell line with the fluorescence-labeled HEL1 by using under confocal microscope;
HEL1: experimental group using *Hericium erinaceum* HEL1 lectin;
SNA: positive control using Sambucus nigra (SNA) lectin; and BSA: negative control using bovine serum albumin (BSA).

SEQUENCE LISTING

The Sequence Listing is submitted as an ASCII text file [7037-96952-01_Sequence_Listing.txt, Mar. 16, 2018, 4.44 KB], which is incorporated by reference herein.

DESCRIPTION OF THE PREFERRED EMBODIMENTS

Hereinafter, the present invention is described in detail.

The present invention provides a *Hericium erinaceum* NEU-1L strain deposited under the deposit number KCTC 12499BP that can produce a lectin binding specifically to sialic acid moieties.

The said strain is preferably composed of the 26S rDNA nucleotide sequence represented by SEQ. ID. NO: 1 and the ITS1-5.8S-ITS4 rDNA nucleotide sequence represented by SEQ. ID. NO: 4, but not always limited thereto.

The said lectin protein binding specifically to sialoglycoconjugates is preferably binding to N-linked glycan structures or O-linked glycan structures in a fetuin glycoprotein added with sialic acid, but not always limited thereto.

In a preferred embodiment of the present invention, the inventors isolated a novel strain from *Hericium erinaceum* obtained from a mushroom farm in order to investigate the lectin binding specifically to sialic acid sugar chains, and further analyzed 26S rDNA and 5.8S rDNA sequences for the molecular biological identification of the strain. As a result, the inventors confirmed that the 26S rDNA sequence of the strain was same as the sequence represented by SEQ. ID. NO: 1 (see Table 1). Then, the relationship of the 26S rDNA composed of the sequence represented by SEQ. ID. NO: 1 with similar species was investigated. As a result, it was confirmed from the comparison of the strain of the invention with *Hericium erinaceum* 5.8S ribosomal RNA and *Hericium erinaceum* 18S ribosomal RNA that the sequence identity was 98% with both (see FIG. 1). Therefore, the strain of the invention was named '*Hericium erinaceum* NEU-1L', which was deposited at Korean Collection for Type Cultures (KCTC), Korea Research Institute of Bioscience and Biotechnology (KRIBB), on Oct. 4, 2013 (KCTC 12499BP).

The present invention also provides a method for preparing a lectin, which binds specifically to sialic acid sugar chains, and is or can be separated from *Hericium erinaceum* NEU-1L strain, the method comprising the following steps:

(a) obtaining a cell extract from the fruiting body of the *Hericium erinaceum* NEU-1L strain deposited under the deposit number KCTC 12499BP; and (b) purifying a lectin from the cell extract above by using the column filled with the resin conjugated with glycoproteins, glycopeptides, glycolipids, oligosaccharides, or monosaccharides containing sialic acid moieties.

It is preferred to include an additional step of isolation of a target lectin selectively from the lectin purifying in step (b) above by interrupting the lectin bound to glycan moieties in the glycoconjugate-immobilized or linked resins, but not always limited thereto.

In a preferred embodiment of the present invention, an extract was prepared in order to isolate a lectin from the *Hericium erinaceum* fruiting body. To purify the lectin, Fetuin-agarose column chromatography was performed with the extract prepared above. As a result, the lectin protein bound to the sialoglycoprotein fetuin was eluted.

The present invention also provides a lectin binding specifically to sialic acid moieties prepared by the method of the invention.

The present invention also provides a lectin binding specifically to sialic acid moieties and having the molecular weight of 15 kDa~20 kDa, which is produced from the *Hericium erinaceum* NEU-1L strain deposited under the deposit number KCTC 12499BP and includes the protein N-terminal amino acid sequences represented by SEQ. ID. NO: 7, NO: 8, or NO: 9.

The present invention also provides a lectin binding specifically to sialic acid moieties and having the molecular weight of 50 kDa~75 kDa, which is produced from the *Hericium erinaceum* NEU-1L strain deposited under the deposit number KCTC 12499BP and includes the protein N-terminal amino acid sequences represented by SEQ. ID. NO: 9.

The present invention also provides a lectin characteristically binding to the glycan structure selected from the group composed of the followings;

sialylated glycan wherein NeuAc or NeuGc($\alpha$2,3) is added to Gal or Glc residue;

sialylated glycan wherein NeuAc or NeuGc($\alpha$2,6) is added to Gal or Glc residue;

sialylated glycan wherein NeuAc or NeuGc($\alpha$2$\rightarrow$3) is added to Gal($\beta$1$\rightarrow$4)Glc or Glc($\beta$1$\rightarrow$4)Glc residue;

sialylated glycan wherein NeuAc or NeuGc($\alpha$2$\rightarrow$6) is added to Gal($\beta$1$\rightarrow$4)Glc or Glc($\beta$1$\rightarrow$4)Glc residue;

sialylated glycan wherein NeuAc or NeuGc($\alpha$2$\rightarrow$3) is added to Gal($\beta$1$\rightarrow$4)GlcNAc or Gal($\beta$1$\rightarrow$3)GlcNAc residue;

sialylated glycan wherein NeuAc or NeuGc($\alpha$2$\rightarrow$6) is added to Gal($\beta$1$\rightarrow$4)GlcNAc or Gal($\beta$1$\rightarrow$3)GlcNAc residue;

sialylated glycan wherein NeuAc or NeuGc($\alpha$2$\rightarrow$3) is added to Gal($\beta$1$\rightarrow$3)[$\alpha$Fuc(1$\rightarrow$4)]GlcNAc residue;

sialylated glycan wherein NeuAc or NeuGc($\alpha$2$\rightarrow$6) is added to Gal($\beta$1$\rightarrow$3)[$\alpha$Fuc(1$\rightarrow$4)]GlcNAc residue;

sialylated glycan wherein NeuAc or NeuGc($\alpha$2$\rightarrow$3) is added to Gal($\beta$1$\rightarrow$4)[$\alpha$Fuc(1$\rightarrow$3)]GlcNAc residue;

sialylated glycan wherein NeuAc or NeuGc($\alpha$2$\rightarrow$6) is added to Gal($\beta$1$\rightarrow$4)[$\alpha$Fuc(1$\rightarrow$3)]GlcNAc residue;

sialylated glycan wherein NeuAc or NeuGc($\alpha$2$\rightarrow$8) is added to NeuAc residue;

sialylated glycan wherein NeuAc or NeuGc($\alpha$2$\rightarrow$8) is added to NeuAc($\alpha$2$\rightarrow$3) Gal($\beta$1$\rightarrow$4)GlcNAc residue;

sialylated glycan wherein NeuAc or NeuGc($\alpha$2$\rightarrow$8) is added to NeuAc($\alpha$2$\rightarrow$8)NeuAc($\alpha$2$\rightarrow$3) Gal($\beta$1$\rightarrow$4)GlcNAc residue;

sialylated glycan wherein NeuAc or NeuGc($\alpha$2$\rightarrow$38) is added to NeuAc($\alpha$2$\rightarrow$8) [NeuAc($\alpha$2$\rightarrow$8)]nNeuAc($\alpha$2$\rightarrow$3) Gal($\beta$1$\rightarrow$4)GlcNAc residue; and sialylated glycan wherein NeuAc or NeuGc($\alpha$2$\rightarrow$8) is added to [NeuAc]n residue.

The present invention also provides a kit containing the lectin of the invention for the measurement or quantification of glycoconjugates such as glycoproteins, glycopeptides, glycolipids, sugar precursors, or oligosaccharides having sialic acid moieties.

The present invention also provides a kit containing the lectin of the invention for the monitoring, measurement, or quantification of cell lines, bacteria, or viruses having sialoglycoconjugates on their surface thereof.

The present invention also provides a method for the measurement or quantification of the sialoglycocconjugates such as the glycoproteins, glycopeptides, glycolipids, sugar precursors, or oligosaccharides having sialic acid sugar chains, which comprises the following steps:

a) contacting a test sample to the lectin of the invention; and b) analyzing the glycoproteins, glycopeptides, glycolipids, sugar precursors, or oligosaccharides binding to the lectin above.

The present invention also provides a method for the measurement or quantification of the cell lines, bacteria, or viruses having sialic acid sugar chains, which comprises the following steps:

a) contacting a test sample to the lectin of the invention; and b) analyzing the cell lines, bacteria, or viruses binding to the lectin above.

In a preferred embodiment of the present invention, the eluted protein was concentrated by using Amicon®Ultra Centrifugal filter 10K. The purified proteins' molecular weight and their purity were checked by SDS-PAGE, followed by Coommassie Brilliant Blue staining. As a result, the lectins bound to the sialoglycoconjutes were purified by using fetuin agarose column. The purified lectins were identified as HEL1 and HEL2 and the molecular weights of these two kinds of proteins were approximately 15~20 kDa and 50~75 kDa (see FIG. 2). The purication procedure optimization was completed with these two lectin proteins, HEL1 and HEL2. As a result, the pure HEL1 and HEL2 lectin proteins can be purified by using the ion exchange chromatography DEAE-Sepharose column, the affinity chromatography fetuin column, and the size exclusion chromatography Superose 12 10/300 GL column. The molecular weight of each protein was approximately 15~20 kDa and 50~75 kDa (see FIG. 3). To measure the precise molecular weight of each protein separated above, Microflex Maldi-TOF MS (Bruker Daltonik GmbH. Bremen, Germany) was performed. As a result, the molecular weight of each lectin was precisely 15327.587 Da or 15536.953 Da and 73253.12 Da (see FIG. 4). The oligomerized size and pI of HEL1 lectin protein were analyzed under non-denaturing condition. As a result, HEL1 lectin was confirmed as a protein in the structure of 32±5 kDa dimer or tetramer with pI 4.2~4.5 (see FIG. 5). Erythrocyte agglutination was investigated with HEL1 lectin. Test was equally performed with the positive control SNA-1 lectin. As a result, all the erythrocyte samples were aggregated by HEL1. In particular, the agglutination by HEL1 lectin was more active in porcine erythrocytes than in rabbit or human erythrocytes (see FIG. 6). To investigate the binding activity of the lectin, lectin blotting was performed using the fetuin containing sialic acid moieties and the sialic acid-free asialofetuin as the substrates. As a result, lectin blot signal was observed in the fetuin containing such N-linked glycan structure as Neu5Ac α(2,3) Gal β(1,4)GlcNAc and such O-linked glycan structure as Neu5Ac α(2,3)Gal β(1,3)[GalNA, Neu5Acα(2,3)Galβ(1,4) Galβ(1,6)]. However, lectin blot signal was not observed in the negative control protein asialofetuin containing N-linked glycan structure as Galβ(1,4)GlcNAc and O-linked glycan as Neu5Ac α(2,3)Galβ, Neu5Ac α(2,3)Galβ(1,3) GalNA, Neu5Ac α(2,6)[Galβ(1,3)]GalNA, Neu5Acα(2,3)Galβ(1,3) [Neu5Ac α(2,6)]GalNAc], Neu5Acα(2,3)Galβ(1,3) [Neu5Ac α(2,3)Galβ(1,4)GlcNAcβ(1,6)]GalNAc (see FIG. 7). In addition, the surface of A549 cell line containing the sialoglycoconjugates identified on animal cell surface was observed by using a fluorescence-labeled lectin. As a result, the fluorescence-labeled lectin can be recognizable for detection of the surface of the cell line, confirming the existence of its sialoglycoconugates (see FIG. 8).

The present invention provides a method for producing a lectin, which binds specifically to sialoglycoconjugates, from a fruiting body of a novel *Hericium erinaceum* (deposit number: KCTC 12499BP) NEU-1L strain; and a lectin produced thereby. The lectin of the present invention can be useful as an active ingredient of a composition or a kit for measuring or detecting glycoproteins, glycopeptides, glycolipids, sugar precursors or oligosaccharides harboring sialic acid moieties, or a composition or a kit for measuring or detecting cell lines, bacteria and viruses containing sialoglycoconjugates.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Isolation and Identification of a Lectin from the Fruiting Body of a Mushroom Strain <1-1> Isolation of the Mushroom Strain for a Lectin Purification The following experiment was performed to isolate a novel strain from *Hericium erinaceum* purchased from Dolsan mushroom farming association (Jeollanam-do Yeosu-si Dolsan-eup Geumbong-ri 1156).

Particularly, spores were obtained from the sporocyst of *Hericium erinaceum* purchased from Dolsan mushroom farming association by using a platinum loop. The obtained spores were distributed on solid media such as PDA, YDP, and amino acid minimal medium, followed by static culture at 22° C. After culturing at least 10 days, the hyphae produced from a single cell were isolated for pure culture, which were inoculated again on the same medium as the above, followed by static culture at 22° C. Then, the pure culture of the mushroom was confirmed by observing the morphology.

<1-2> Molecular Identification of a Lectin Producing Mushroom Strain

To identify the strain isolated in Example <1-1> molecular-biologically, 26S rDNA and 5.8S rDNA sequencing was performed.

Particularly, the strain isolated in Example <1-1> was inoculated in each liquid medium of 10 mL PDA, 10 mL YDP, and 10 mL amino acid minimal medium in a 125 ml flask, followed by static culture at 22° C. After culturing the strain for at least 15 days, the cells were harvested, followed by centrifugation. The liquid medium was discarded. The harvested cells were frozen under liquid nitrogen and then lysed physically. The lysed cells were added with cell lysis buffer containing 50 mU/mL Lypticase, 50 mM Tris-HCl (pH 8.0), and 250 mM NaCl, followed by reaction at 37° C. for at least 1 hour. Upon completion of the reaction, the whole cell lysates were centrifugated and then intracellular DNA was extracted by using AccuPrep®Genomic DNA Extraction Kit (Bioneer, Daejeon, Korea). To amplify 26S rDNA, DNA polymerase chain reaction was performed with 30 cycles of 94° C. for 45 seconds; 55° C. for 1 second; and 72° C. for 1 minute and seconds by using the extracted DNA above as a template with NL1 primer (SEQ. ID. NO: 2) and LR6 primer (SEQ. ID. NO: 3). As a result, 1,146 by gene was amplified. The amplified gene was cloned in pGEM-T easy vector (Promega, USA), followed by sequencing. The nucleotide sequence of 26S rDNA of the strain was identified as the sequence represented by SEQ. ID. NO: 1 as shown in Table 1 below (Table 1). Then, the evolutionary relationship of the 26S rDNA sequence represented by SEQ. ID. NO: 1 with similar species was analyzed. As a result, a phylogenetic tree analysis shows the strain of the invention is clusted with 5.8S and 18S ribosomal RNA coding DNA sequences of other *Hericium* species such as *Hericium erinaceum, Hericium coralloides, Hericium abietis, Hericium americanum,* and *Hericium alpestre.* However the strain of the invention is a different mushroom specie with 98% sequence identity among *Hericium* species cluster family (FIG. 1). Therefore, the strain obtained above was named '*Hericium erinaceum* NEU-1L', which was deposited at Korean Collection for Type Cultures (KCTC), Korea Research Institute of Bioscience and Biotechnology (KRIBB), on Oct. 4, 2013 (KCTC 12499BP). To analyze ITS1-5.8S-ITS4 rDNA sequence of the *Hericium erinaceum* NEU-1L strain, DNA polymerase chain reaction was performed with 30 cycles of 94° C. for 45 seconds; 55° C. for 30 seconds; and 72° C. for 1 minute and 30 seconds by using ITS1 primer (SEQ. ID. NO: 5) and ITS4 primer (SEQ. ID. NO: 6, 5'-TCCTCCGCTTATTGATATGC-3'). As a result, 644 bp gene was amplified. The amplified gene was cloned in pGEM-T easy vector, followed by sequencing. As a result, it was confirmed that the gene was composed of the sequence represented by SEQ. ID. NO: 4 (Table 1).

TABLE 1

| SEQ. ID. NO | Sequence |
| --- | --- |
| 26S rDNA sequence (SEQ. ID. NO: 1) | 5'-ACTAGTGATTCGCCAGTTCTGCTTACCAAAAATGGCCCACT AGAAACTCTCAATCGCCAAGCGGTCCAATCAAGTGACGGCT TGTTCTTACATATTTAAAGTTTGAGAATAGGTTAAGGTTGT TTCAACCCCAAGGCCTCTAATCATTCGCTTTACCACATAAA TCTGATATGAGTTTCTGCTATCCTGAGGGAAACTTCGGCAG GAACCAGCTACTAGATGGTTCGATTAGTCTTTCGCCCCTAT ACCCAAATTTGACGGTCGATTTGCACGTCAGAATCGCTACG AGCCTCCACCAGAGTTTCCTCTGGCTTCACCCTATTCAGGC ATAGTTCACCATCTTTCGGATCCCAACATACACGCTCTACC GCAGATCCGTCACAGAAGGTCTGGTCCGGGCGTCGGTGCCC TCCATAACAGAGGTCCCAACTTTCACTTTCATTACGCGCAC GGGTTTTCCACCCGAACACTCGCGGGCATGTTAGACTCCTT GGTCCGTGTTTCAAGACGGGTCGTTTAAAGCCATTACGCCA GCATCCTAAGCATGAACGTGGGCGAACCCCGACCATAAAGG CATGCTGAATTCCTCAATCCCAACCACCGTATACGACTGGA GGCTATAACACACCCGAAGGTGCCACATTCCCCCAGCCCTT GTCCGGCAGTCGAAATTGATGCTGGCCCGTCCACCAGAAAA TACACCAGGCAAGATTGCAAGGCTGAGTTCTGGCGGACGCG ACTGACTTCAAGCGTTTCCCTTTCAACAATTTCACGTACTG TTTAACTCTCTTTCCAAAGTGCTTTTCATCTTTCCCTCACG GGTACTTGTTCGCTATCGGGTCTCTCGCCAATATTTAGCTT TAGATGAATTCACCACCCATTTTGAGCTGCATTCCCAAAC AACTCGACTCTTTGAGAGCGCATCACAGAGCACTGGTAGTC CGTGTCAAAGACGGGATTCTCACCCTCTATGACGCTCCATT CCAGGAGACTTGTACACGGTCCAGCGCGGAAAGCACTTCTC CAGACTACAACTCGGACGGCCAAAGACCGCCAGATTTTAAA TTTGAGCTTTTCCCGCTTCACTCGCAGTTACTAGGGGAATC CTTGTTAGTTTCTTTTCATCCGCTTATTGATATGCAATC-3' |
| NL1 primer (SEQ. ID. NO: 2) | 5'-GCATATCAATAAGCGGAGGAAAAG-3' |
| LR6 primer (SEQ. ID. NO: 3) | 5'-CGCCAGTTCTGCTTACC-3' |
| ITS1-5.8S-ITS4 rDNA | 5'-ACTAGTGATTTCCGTAGGTGAACCTGCGGAAGGATCATTAA TGAATTTGAAAGGAGTTGTTGCTGGCCTGAAACCCAGGCAT |

TABLE 1-continued

| SEQ. ID. NO | Sequence |
| --- | --- |
| sequence (SEQ. ID. NO: 4) | GTGCACGCTCCAATCTCATCCATCTTACACCTGTGCACCCT TGCGTGGGTCCGTCGGCTTTGCGGTCGATGGGCTTGCGTTT TTCATAAACTCTTATGTATGTAACAGAATGTCATAATGCTA TAAACGCATCTTATACAACTTTCAACAACGGATCTCTTGGC TCTCGCATCGATGAAGAACGCAGCGAAATGCGATAAGTAAT GTGAATTGCAGAATTCAGTGAATCATCGAATCTTTGAACGC ACCTTGCGCCCCTTGGTATTCCGAGGGGCACGCCTGTTCGA GTGTCGTGAAATTCTCAACTCAATCCTCTTGTTATGAGAGG GCTGGGCTTGGACTTGGAGGTCTTGCCGGTGCTCCCTCGGG AAGTCGGCTCCTCTTGAATGCATGAGTGGATCCCTTTTGTA GGGTTTGCCCTTGGTGTGATAATTATCTACGCCGCGGGTAG CCTTGCGTTGGTCTGCTTCTAACCGTCTTCGGACAACTTTC ATCTCAACTTGACCTCGAATCAGGCGGGACTACCCGCTGAA CTTAAGCATATCAATAAGCGGAGGAAATC-3' |
| ITS1 primer (SEQ. ID. NO: 5) | 5'-TCCGTAGGTGAACCTGCGG-3' |
| ITS4 primer (SEQ. ID. NO: 6) | 5'-TCCTCCGCTTATTGATATGC-3' |

Example 2: Isolation and Purification of a Sialoglycoconjugate-Binding Lectin from *Hericium erinaceum*

<2-1> Preparation of an Extract for the Separation of a Lectin from the *Hericium erinaceum* Fruiting Body The following experiment was performed to prepare an extract for the isolation of a lectin from the *Hericium erinaceum* fruiting body.

Particularly, the *Hericium erinaceum* fruiting body stored as frozen at −80° C. was placed in a mortar, followed by grinding the fruiting body with adding liquid nitrogen in order for the fruiting body not to be thawed. The fruiting body was prepared as frozen fine powder through a series of grinding process in the mortar. The prepared fruiting body frozen powder was harvested and stored at −80° C. again until it would be used for the experiment. After measuring the weight of the fruiting body frozen powder prepared by the method above, protease inhibitor cocktail (Roche, Switzerland) was added thereto at the volume of three times the weight of the fruiting body together with 20 mM Tris-HCl buffer (pH 8.0) containing 1 mM PMSF at the volume of three times the volume of the fruiting body. The mushroom fruiting body extract was well mixed at 4° C. for at least 6 hours. To discard the non-grinded fruiting body particles and insoluble proteins, the extract was centrifugated by using SUPRA 22K centrifuge (Hanil Science Inc., Korea) equipped with A500S-6N rotor (Hanil Science Inc., Korea) at 4° C., 7,000 rpm for 30 minutes. Then, the precipitates were discarded and the supernatant was obtained. The obtained supernatant was re-centrifugated at 4° C., 12,000 rpm for 30 minutes. Then, the precipitate was discarded and the supernatant was obtained as the crude protein extract for the lectin purification.

<2-2> Purification of a Lectin by Fetuin-Agarose Column Chromatography

To purity a lectin by using the extract obtained by the method of Example <2-1>, Fetuin-agarose column chromatography was performed.

Particularly, in order to purify the lectin binding specifically to sialic acid, a column for the lectin purification was prepared with Fetuin-agarose, an agarose resin on which fetuin was immobilized. The *Hericium erinaceum* fruiting body cell extract prepared by the method of Example <1-1> was applied into the Fetuin-agarose resin (Sigma-Aldrich, USA) packed column (1.0×10 cm) equilibrated with 20 mM Tris-HCl buffer (pH 8.0) by using Pump P-1 peristatic pump (GE Healthcare, USA) at the flow rate of 1 mL/min. The column was washed with the same buffer of 10 times column. Then, proteins bound to fetuin column was eluted with a step gradient at 20 mM via 40 mM upto 200 mM galactose. At that time, the elution flow rate was 1 ml/min. The eluted protein was concentrated by using Amicon® Ultra Centrifugal filter 10K.

<2-3> Identification of a Lectin Protein by SDS-PAGE

To confirm the lectin protein purified from the mushroom fruiting body lysate by the method of Example <2-2>, the following experiment was performed.

Particularly, the fractions obtained in each steps by the same procedure as described in Example <2-2> was analyzed by SDS-PAGE, followed by staining with Coommassie Brilliant Blue. As a result, as shown in FIG. 2, two proteins were dominantely eluted from the mushroom lysate by using Fetuin-agarose column: Fetuin-affinity proteins were identified as HEL1 and HEL2 and the size of these two kinds of proteins were approximately 15~20 kDa for HEL1 and 50~75 kDa for HEL2(FIG. 2).

<2-4> Optimization of Purification Procedure for HEL1 Lectin Protein from the *Hericium erinaceum* Fruiting Body The following experiment was performed to provide the optimized purification procedure for HEL1 and HEL2 lectin proteins identified in Example <2-2> by using the extract prepared by the method of Example <2-1>.

Particularly, after measuring the weight of the fruiting body frozen powder prepared and stored as described in Example <2-1>, 50 mM Tris-HCl (pH 7.4) was added thereto at the volume of 2.5 times the weight of the fruiting body powder, which was well mixed at 4° C. for at least 12 hours. To eliminate the non-grinded fruiting body particles and insoluble proteins from the mixture, centrifugation was performed at 4° C., 20,000×g, for 30 minutes. Then, the precipitate was eliminated and the supernatant was obtained. To eliminate the remaining unwanted particles completely, centrifugation was performed again at 4° C., 25,000×g, for 45 minutes. Then, the precipitate was discarded and the supernatant was obtained again. The same buffer was added to the precipitated fruiting body at the volume of 1.5 times the weight of the fruiting body. The supernatant was obtained from the mixture by the same manner as described above. Each supernatant obtained above was mixed together to prepare the mushroom extract. Ammonium sulfate (saturation concentration 80%) was added thereto, which was stirred slowly at 4° C. to precipitate protein. The mixture was centrifuged at 4° C., 25,000×g, for 60 minutes to obtain the precipitate protein. The obtained protein was dissolved in 50 mM Tris-HCl (pH 7.4) buffer (1/10 v/v), followed by dialysis in the same buffer or passing through PD-10 deslating column (GE Healthcare) in order to eliminate ammonium sulfate from the crude extract.

After desalting, the crude extract was applied into DEAD-Sepharose column (1.5×17 cm), followed by column equilibration with 50 mM Tris-HCl (pH 7.4) buffer 5 times column volume. 50 mM Tris-HCl (pH 7.4) buffer containing 0~0.5 M NaCl was applied in a step gradient or a linear gradient by using AKTA purification system (GE Healthcare) to elute the lectin protein from the column. The fraction containing lectin activity was analyzed by agglutination assay with 0.5% (v/v) porcine erythrocytes. The fractions were collected, pooled together and then concentrated by using Amicon® Ultra Centrifugal filter 10K.

The concentrated protein pool was loaded in the Fetuin-agarose resin (Sigma-Aldrich, USA) column (1.5×17 cm) equilibrated with 50 mM Tris-HCl (pH 7.4) buffer by the same manner as described in Example <2-2>. The column was washed with the same buffer of 10 times column volume. After washing, fetuin-bound proteins were eluted by using the same buffer containing 0.2~0.5 M D-galactose. The eluted protein fractions were concentrated.

The concentrated protein solution showing agglutination activity was loaded in Superose 12 10/300 GL (GE Healthcare) chromatography column equilibrated with 50 mM Tris-HCl buffer (pH 7.4). The protein was eluted by using AKTA purification system at the flow rate of 0.5 mL/min. Finally, the fractions confirmed positive to the porcine erythrocyte agglutination assay were pooled together and then concentrated.

The lectin protein fractions obtained from each step were separated by 12% or 15% SDS-PAGE by the same manner as described in Example <2-3>.

As a result, as shown in FIG. 3, the pure HEL1 and HEL2 lectin proteins were purified through ion exchange chromatography DEAE-Sepharose column, affinity chromatography fetuin column, and size exclusion chromatography Superose 12 10/300 GL column. The molecular weights of HEL1 and HEL2 were approximately 15~20 kDa and 50~75 kDa, respectively (FIG. 3).

Example 3: Determination of N-Terminal Amino Acid Sequences of the Lectin Protein Purified from the *Hericium erinaceum* Fruiting Body To determine the amino acid sequence of the lectin protein binding selectively to sialic acid isolated from the *Hericium erinaceum* fruiting body by the method of Example <2-4>, the N-terminal amino acid sequences was analyzed as follows.

Particularly, the lectin protein prepared by the method of Example <2-4> was separated by using 16% Tricin-PAGE. The protein on Tricin-PAGE was transferred onto PVDF membrane by using Trans-Blot SD Semi-Dry Transfer Cell (Bio-Rad, USA) at 15 V for 1 hour. The protein transferred onto PVDF membrane from Tricin-PAGE was stained with 0.1% (w/v) Ponceau S. The stained protein was cut off from the membrane, which N-terminal sequence of the lectin protein was analyzed at eMass Co. (Seoul, Korea).

As a result, the HEL1 protein with the molecular weight of 15~20 kDa was identified the two amino acid sequences as HEL1a and HEL1b: HEL1a displaying a strong signal was identified as the N-terminal sequence represented by SEQ. ID. NO: 7 (NH2-KEPTVWGRPES-$CO2^-$). However HEL1b displaying a rather weak signal was identified as the N-terminal sequence represented by SEQ. ID. NO: 8 (NH2-WPVAPDYPPES-$CO2^-$). In addition, the protein in the molecular weight of 50~75 kDa was confirmed to have the N-terminal sequence represented by SEQ. ID. NO: 9 (NH2-GGHSVPLINFMNAQYFTEISLGSPPQQFKV-$CO_2^-$).

Example 4: Analysis of the Molecular Weight of the Lectin Proteins Using Mass Spectrometer To determine the precise molecular weight of the protein separated by the method of Example <2-4>, Microflex Maldi-TOF MS analysis (Bruker Daltonik GmbH. Bremen, Germany) was performed.

Particularly, the lectin protein purified by the method of Example <2-4> was applied into PD-10 column (GE Healthcare, USA), followed by elution using distilled water to eliminate salts from the protein solution. And then concentrated upto 1 mg/ml proteiin. Then, sinapinic acid was dissolved to be saturated in the solution containing both 25% acetonitrile and 0.1% trifluoroacetic acid with the ratio of 1:2. The sinapinic acid matrix solution was mixed with the concentrated protein at the ratio of 1:1 (v/v), followed by crystallization on MALDI-TOF MS target. The crystallized protein proceeded to Microflex Maldi-TOF MS (Bruker Daltonik GmbH. Bremen, Germany). The molecular weights of the purified lectins were analyzed.

As a result, the molecular weight of HEL1a lectin displaying as strong signal intensity as 5 times the signal of HEL1b was 15327.587 Da. However the molecular weight of HEL1b lectin displaying a weak signal intensity was 15536.953 Da (FIG. 4). In addition, the molecular weight of HEL2 lectin was confirmed to be 73253.12 Da.

Example 5: Analysis of the Molecular Weight and the pI of HEL1 Lectin Protein Under Non-Denaturing Condition The oligomerization of HEL1 lectin protein prepared by the method of Example <2-4> under non-denaturing condition was analyzed by using AKTA purification system equipped with Superose 12 10/300 GL column. As the standard proteins of molecular weight calibration kit (GE Healthcare), 440 kDa ferrtin, 158 kDa aldose, 44 kDa ovalbumin, 29 kDa carbonic anhydrase, 13.7 kDa ribonuclease A, and 6.5 kDa aprotinin were used. The fractions containing HEL1 lectin protein eluted from Superose 12 10/300 GL column were detected by porcine erythrocyte agglutination assay. The resultant chromatogram was interpreted with those of the standard proteins to measure the comparative molecular weight of the native HEL1.

As a result, as shown in FIG. 5A, HEL1 lectin was confirmed in the form of 32±5 kDa dimer or tetramer in non-denaturing condition (FIG. 5A).

Also, pI of the HEL1 lectin protein separated by the same manner as described in Example <2-4> was investigated by Iso-ElectroFocusing (IEF) electrophoresis. IEF-PAG gel analysis was performed using pI 3-7 IEF-gel system (KOMABIOTECH) in cathode and anode buffers at 100 V for 1 hour, at 200 V for 1 hour, and at 500 V for 30 minutes, and the result was compared with pI of the standard protein. As shown in FIG. 5B, HEL1 lectin was confirmed as the protein of pI 4.2-4.5 (FIG. 5B).

Example 6: Test of the Agglutination Activity

To test of the agglutination activity of HEL1 lectin prepared by the method of Example <2-4> towards various erythrocyte derived from porcine blood, rabbit blood, and human blood (B-type) were diluted in 10% (v/v) PBS (phosphate buffer saline), followed by centrifugation at 4° C., 1000 rpm for 5 minutes. As a result, erythrocytes were precipitated. The supernatant was eliminated. The procedure above was repeated three times. The final precipitate was diluted in PBS, resulting in the preparation of 2% (v/v) erythrocyte solution. Agglutination assay was performed using V-shaped 96-well plate. 100 uL of the lectin protein (0.1 mg/mL) prepared in Example <2-4> was serially diluted at the ratio of 1/2, which was mixed with the equal volume of the 2% erythrocyte solution. The mixture in the 96-well plate stood at room temperature for 1 hour. Lectin mediated agglutination of porcine erythrocytes, rabbit erythrocytes, and human erythrocytes were observed. At that time, as the positive control, SNA-I lectin binding selectively to sialic acid sugar chains was used at the same concentration. As the negative control, lectin-free PBS was used.

As a result, as shown in FIG. 6, HEL1 lectin induced erythrocyte agglutination in all the test samples as equally as the positive control SNA-1 lectin did. In particular, the agglutination in porcine erythrocytes by HEL1 was stronger than in rabbit erythrocyte and in human erythrocyte (FIG. 6).

Example 7: Detection of Glycoprotein Containing Sialic Acid Sugar Chain by Lectin Blotting To determine the glycan binding activity of the lectin separated by the method of Example <2-4>, lectin blotting was performed using fetuin containing sialoglycoconjugates and sialic acid-free asialofetuin as substrates.

Particularly, each glycoprotein solution respectively containing fetuin and asialofetuin was mixed with 5× Laemmli buffer, followed by heating for minutes. Electrophoresis was performed using 8% SDS-PAGE gel for the protein separation. The proteins separated on SDS-PAGE gel were transferred onto nitrocellulose membrane at 15 V for 1 hour by using Trans-Blot SD Semi-Dry Transfer Cell (Bio-Rad, USA), followed by blocking with phosphate buffered saline (PBS) comprising 3% bovine serum albumin (BSA), phosphate buffered saline containing tween 20 (PBST), and 0.5% tween for 1 hour. Then, the membrane was loaded in 3% BSA-PBS containing 1 mg/mL of biotin-conjugated lectin, followed by culture at room temperature for 4 hours. The biotinylation conjugation of the lectin was performed by using Antibody Biotinylation Kit (Genomine, KOREA). After the incubation of the biotinylated lectin together with the membrane, the membrane was washed with PBST 6 times for 10 minutes, which was then reacted with 0.2 mg/mL of horseradish peroxidase (HRP) conjugated anti-biotin antibody (1:500, Sigma-Aldrich) for 1 hour. Upon completion of the reaction, the membrane was washed again with PBST 6 times for 10 minutes by the same manner as described above. The sialylated protein was confirmed by using ECL kit (GE Healthcare, USA).

As a result, as shown in FIG. 7, lectin blot signal was observed in the fetuin containing N-linked glycan structure such as Neu5Ac α(2,3) Galβ(1,4)GlcNAc and O-linked glycan structure such as Neu5Ac α(2,3)Galβ, Neu5Ac α(2,3) Galβ(1,3) GalNA, Neu5Ac α(2,6) [Galβ(1,3)]GalNA, Neu5Acα(2,3) Galβ(1,3) [Neu5Ac α(2,6)]GalNAc], Neu5Acα(2,3) Galβ(1,3) [Neu5Ac α(2,3)Galβ(1,4) GlcNAcβ(1,6)]GalNAc. However, the lectin blot signal was not observed in the asialofetuin proteins containing non-sialylated N-linked glycan such as Galβ(1,4)GlcNAc and O-linked glycan such as Galβ, Galβ(1,3) GalNA, Galβ(1,3) GalNA, Galβ(1,3) [Galβ(1,4)GlcNAcβ(1,6)]GalNAc (FIG. 7).

Example 8: Monitoring Animal Cell Surface Containing Sialoglycoconjugates by Using a Fluorescence-Labeled Lectin HEL1 was also applied to be monitoring a live animal cell line containing sialoglycoconjugates on its cell surface. The surface of A549 cell line (ATCC CCL-185TM, Rockville Md., USA) was observed by using a fluorescence-labeled lectin.

Particularly, A549 cell line was cultured in serum-free medium and then harvested by centrifugation. The lectin prepared by the method of Example <2-4> was labeled with a fluorescent material by using Alexa Fluor®488 Protein Labeling Kit (Invitrogen, USA) according to the conventional method well-known to those in the art. The harvested cells were washed with PBS containing 1 mg/mL BSA, followed by centrifugation. The obtained cells were suspended in a small amount of PBS containing BSA (PBSB), and the lectin conjugated with Alexa Fluor®488 was added thereto at the final concentration of 0.5 nM~1.0 nM. The cells were reacted with the fluorescence-labelled lectin on ice for 1 hour. After the one-hour incubation, the cells were centrifuged, washed with PBSB at least three times and then suspended in the same buffer at the final density of $1~5\times10^6$ cells/mL. The fluorescence image of the cells was observed under Zeiss LSM510 Confocal Laser Scanning Microscope (Carl Zeiss Germany).

As a result, as shown in FIG. 8, the fluorescence-labeled lectin can show clearly A549 cell line like that of SNA lectin used in a positive control (FIG. 8). The fluorescence cell image represented HEL1 was usedful to detect sialoglycoconjugates on the cell surface, comparable to other lectins such as SNA and MAA.

DEPOSIT NUMBER

Depositary Authority: Korea Research Institute of Bioscience and Biotechnology
Deposit Number: KCTC 12499BP
Deposit Day: 20131004

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for measurement or quantification of a sialylated conjugate composed of glycoproteins, glycopeptides, glycolipids, sugar precursors, or oligosaccharides having sialic acid moieties, the method comprising the following steps:
   a) contacting a test sample comprising the sialylated conjugate with a lectin which is or can be obtained from a *Hericium erinaceum* NEU-1L strain deposited under the deposit number KCTC 12499BP, wherein the lectin is obtained by
      (i) preparing a crude extract from the fruiting body of the *Hericium erinaceum* NEU-1L strain; and
      (ii) purifying the lectin from the crude extract by using a resin immobilized with one or more of glycoproteins, glycopeptides, glycolipids, oligosaccharides, or monosaccharides,
   wherein the lectin comprises the protein N-terminal sequence of SEQ ID NO: 7 or NO: 8, and has a molecular weight of 15 kDa~20 kDa, or wherein the lectin comprises the protein N-terminal sequence of SEQ ID NO: 9, and has a molecular weight of 50 kDa~75 kDa.; and
   b) measuring or quantifying the glycoproteins, glycopeptides, glycolipids, sugar precursors, or oligosaccharides binding to the lectin.

2. The method of claim 1, wherein the test sample comprises cells, bacteria, or viruses comprising the sialylated conjugate on their surface, and wherein the method further comprises:
   c) measuring or quantifying the cells, bacteria, or viruses binding to the lectin.

3. The method of claim 1, wherein the lectin is provided in a kit.

4. The method of claim 2, wherein the lectin is provided in a kit.

5. The method of claim 1, wherein the lectin binds specifically to one or more of the following glycan structures:
   sialylated glycan wherein NeuAc or NeuGc($\alpha2\rightarrow3$) is added to a Gal or Glc residue;
   sialylated glycan wherein NeuAc or NeuGc($\alpha2\rightarrow6$) is added to a Gal or Glc residue;
   sialylated glycan wherein NeuAc or NeuGc($\alpha2\rightarrow3$) is added to a Gal($\beta1\rightarrow4$)Glc or Glc($\beta1\rightarrow4$)Glc residue;
   sialylated glycan wherein NeuAc or NeuGc($\alpha2\rightarrow6$) is added to a Gal($\beta1\rightarrow4$)Glc or Glc($\beta1\rightarrow4$)Glc residue;
   sialylated glycan wherein NeuAc or NeuGc($\alpha2\rightarrow3$) is added to a Gal($\beta1\rightarrow4$)GlcNAc or Gal($\beta1\rightarrow3$)GlcNAc residue;
   sialylated glycan wherein NeuAc or NeuGc($\alpha2\rightarrow6$) is added to a Gal($\beta1\rightarrow4$)GlcNAc or Gal($\beta1\rightarrow3$)GlcNAc residue;
   sialylated glycan wherein NeuAc or NeuGc($\alpha2\rightarrow3$) is added to a Gal($\beta1\rightarrow3$)[$\alpha$Fuc($1\rightarrow4$)]GlcNAc residue;
   sialylated glycan wherein NeuAc or NeuGc($\alpha2\rightarrow6$) is added to a Gal($\beta1\rightarrow3$)[$\alpha$Fuc($1\rightarrow4$)]GlcNAc residue;
   sialylated glycan wherein NeuAc or NeuGc($\alpha2\rightarrow3$) is added to a Gal($\beta1\rightarrow4$)[$\alpha$Fuc($1\rightarrow3$)]GlcNAc residue;
   sialylated glycan wherein NeuAc or NeuGc($\alpha2\rightarrow6$) is added to a Gal($\beta1\rightarrow4$)[$\alpha$Fuc($1\rightarrow3$)]GlcNAc residue;
   sialylated glycan wherein NeuAc or NeuGc($\alpha2\rightarrow8$) is added to a NeuAc residue;

sialylated glycan wherein NeuAc or NeuGc(α2→8) is added to a NeuAc(α2→3) Gal(β1→4)GlcNAc residue;
sialylated glycan wherein NeuAc or NeuGc(α2→8) is added to a NeuAc(α2→8)NeuAc(α2→3) Gal(β1→4)GlcNAc residue;
sialylated glycan wherein NeuAc or NeuGc(α2→8) is added to a NeuAc(α2→8) [NeuAc(α2→8)]nNeuAc (α2→3) Gal(β1→4)GlcNAc residue; and
sialylated glycan wherein NeuAc or NeuGc(α2→8) is added to a [NeuAc]n residue.

* * * * *